United States Patent [19]
Almond et al.

[11] Patent Number: 4,916,218
[45] Date of Patent: Apr. 10, 1990

[54] 1-(β-D-XYLOFURANOSYL)THYMINE DERIVATIVES

[76] Inventors: Merrick R. Almond, 1214 Chimney Hill Dr., Apex, N.C. 27502; Jeffrey D. Wilson, 27 Gorham Pl., Durham, N.C. 27705; Janet L. Rideout, 3101 Morningside Dr., Raleigh, N.C. 27607

[21] Appl. No.: 204,692

[22] Filed: Jun. 9, 1988

[51] Int. Cl.$^4$ .................. C07H 15/00; C07H 17/00
[52] U.S. Cl. ............................ 536/18.2; 536/23; 536/122
[58] Field of Search ................ 536/23, 18.2, 122

[56] References Cited

PUBLICATIONS

Wilson et al., Chem. Abst. 111-23914a.
Watanabe et al., J. Med. Chem., 1980, 23, pp. 1088-1094.
Guiller, A. et al., J. Carbohydrate Chemistry 5(2), 153-160 (1986).
Guiller, A. et al., J. Carbohydrate Chemistry 5(2), 161-168 (1986).
Guiller, A. et al., Carbohydrate Research, vol. 180, No. 2, Sep. 15, 1988, 233-242.
Baraldi et al., J. Med. Chem., 1984, 27, 986-990, Pyrazolo[4.3-d] Pyrimidine Nucleosides . . .
Watanabe et al., J. Med. Chem., 1980, 23, 1088-1094, Nucleosides, 116 . . .
Russell et al., Biochemistry, Dec. 1969, 8(12), vol. 8, No. 12, Synthesis of Some Nucleotides Derived from 3'-Deoxythymidine.
Montgomery et al., J. Carbohydrates-Nucleosides-Nucleotides, 2(2), 147-151 (1975), A Convenient Method for the Preparation of Methyl 2,3-Anhydro-β-D-Ribofuranoside.

*Primary Examiner*—Cecilia Shen
*Attorney, Agent, or Firm*—Donald Brown

[57] ABSTRACT

This invention relates to a new synthetic process for the manufacture of zidovudine from the starting material D-xylose involving:
 (i) Conversion of D-xylose to a 1-(β-D-xylofuranosyl)thymine derivative;
 (ii) 2'-Deoxygenation of the thymine derivative; and
 (iii) 3'-Azidation of the 2'-deoxy compound.

2 Claims, No Drawings

1-(β-D-XYLOFURANOSYL)THYMINE DERIVATIVES

The present invention relates to a novel process for the preparation of 3'-azido-3'-deoxythmidine and to intermediates of use in such a process.

The preparation of 3'-azido-3'-deoxythymidine was first described by J. P. Horwitz et al., J. Org. Chem., 29, 2076–2078, 1964, and later for example by R. P. Glinski et al., J. Org. Chem., 38, 4299–4305, 1973 and T-S Lin et al., J. Med. Chem., 21 1 109–112 1978. More recently, 3'-azido-3'-deoxythymidine has been discovered to have a potent antiviral activity against the human immunodeficiency virus (HIV), and has been reported to be of potential value for the therapeutic treatment of acquired immune deficiency syndrome (AIDS) (R. Yarchoan et al., The Lancet, 1 (8481), 575–580, Mar. 15, 1986). Following further extensive clinical investigation this compound has been found to be of therapeutic benefit in the treatment of AIDS and AIDS-related complex (ARC). 3'-azido-3'-deoxythymidine (otherwise named 1-(3'-azido-2'-3'-dideoxy-D-erythro-pentofuranosyl)-thymine) has recently been given the approved name zidovudine.

In view of the demand for relatively large quantities of zidovudine to fulfil clinical testing requirements and to meet other demands for the compound, considerable effort has been devoted towards ensuring adequate supplies of the compound on an industrial scale. A major difficulty that has been encountered in the commercial manufacture of zidovudine is that previously reported methods for the preparation of zidovudine (on a laboratory scale) have involved the use of thymidine as a starting material or intermediate. However, thymidine is a relatively expensive material and its commercial availability is relatively limited, which consequently limits the supply of zidovudine when prepared by previously reported methods.

We have therefore investigated alternative routes of synthesis for zidovudine starting from other, less expensive and more readily available, starting materials. As a result of considerable research and development, we have now discovered a synthetic route for zidovudine that uses, as a starting material, D-xylose which is a relatively inexpensive and readily commercially available starting material, thus avoiding the use of thymidine.

The new synthetic route is characterised by a sequence of key steps involving certain novel intermediates for example novel 5'-methoxy carbonyl-protected derivatives described in more detail below. These intermediates may then be converted to zidovudine by a series of steps essentially involving 2'-deoxygenation (which may be photolytic in nature); introduction of a leaving group at the 3'-position of the sugar residue and replacement of said leaving group by an azido group.

The overall synthetic route will be described in relation to the key steps referred to above which essentially involve (i) conversion of D-xylose to a 1-(β-D-xylofuranosyl)thymine derivative, (ii) 2'-deoxygenation of the thymine derivative; and (iii) 3'-azidation and 5'-deprotection of the 2'-deoxy compound.

Thus, the key steps, each of which represents a feature of the present invention, comprise:

(i) Conversion of D-xylose to 1-(β-D-xylofuranosyl)thymine derivative (a) treating D-xylose, i.e.

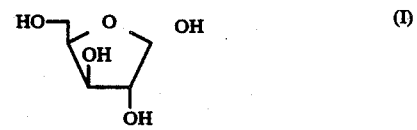

with a selective hydroxy blocking agent to form a compound of formula (II)

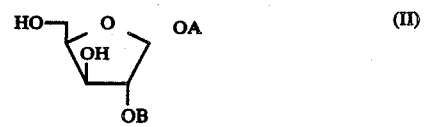

in which A and B each represent a hydroxy blocking group or together form a single such group serving to block the 1- and 2-hydroxy groups;

(b) treating a compound of formula (II) with further hydroxy blocking agents which either selectively block the 5- and/or 3-hydroxy groups or together form a single group blocking the 5- and 3-hydroxy groups;

(i) optionally treating the resulting compound with an agent capable of deblocking the 1- and 2-hydroxy groups and optionally introducing a cyclic sulphite group blocking the 1- and 2-hydroxy groups; or alternatively (ii) treating the resulting compound with an agent serving to introduce a leaving group at the 3-position of the sugar ring and optionally replacing any combined groups blocking the 1- and 2-hydroxy groups with single such blocking groups or a single group blocking the 1-hydroxy group, the 2-hydroxy group being optionally blocked by a photolytically reduceable group; and then (iii) optionally introducing a leaving group at the 1-hydroxy position of the sugar ring.

(c) reacting the resulting compound with a thymine derivative of formula (III)

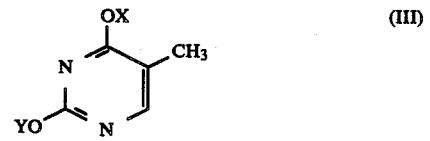

(wherein X and Y each represent an activating group), to form a compound of formula (IV)

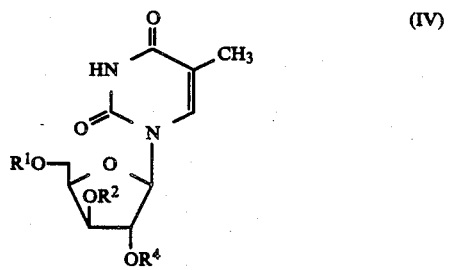

(wherein $R^1$ is a hydroxy blocking group, $R^2$ is a leaving group, or $R^1$ and $R^2$ are individual hydroxy blocking groups or together form a single hydroxy blocking group and $R^4$ is hydrogen or a hydroxy blocking group preferably a photolytically reduceable group).

(ii) 2'-deoxygenation of the thymine derivative (d)

(i) optionally deblocking the 3' and 5'-hydroxy groups and reblocking with alternative blocking groups (wherein $R^4$ is a non-photolytically reduceable hydroxy blocking group, treating a compound of formula (IV) with an agent to remove the 2'-hydroxy blocking group), then treating the 2'-hydroxy compound with an agent serving to provide a photolytically or non-photolytically reduceable group at the 2'-position of the sugar moiety directly, or by:

(1) introducing a leaving group at the 2'-position of the sugar moiety;
(2) cyclising the compound to form a 2',2-anhydro derivative and either
  (a) opening the ring to give a compound of formula (V)a or (V)b;

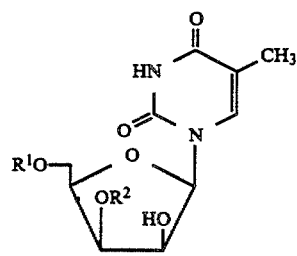

(V)a

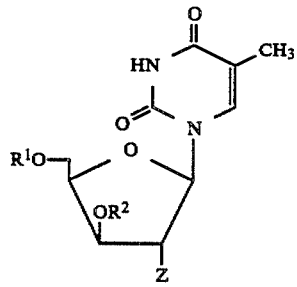

(V)b (wherein $R^1$ and $R^2$ are as hereinbefore defined and Z is a photolytically or non-photolytically reducible group) and introducing a photolytically reducible group at the 2'-position of the sugar ring of structure (V)a; or
  (b) introducing a non-photolytically reduceable group at the 2'-position of the sugar ring, and reducing to form a compound of formula (VI) below.

(ii) reacting a compound of formula (IV) wherein $R^4$ is a photolytically reduceable group or a compound from (d) (i) above to deoxygenate the 2'-position sugar moiety to form a compound of formula (VI);

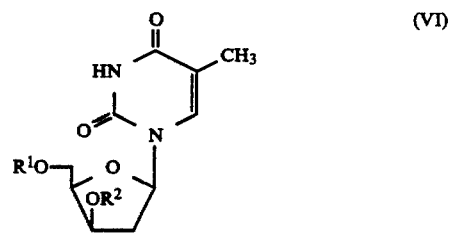

(VI)

(wherein $R^1$ and $R^2$ are as hereinbefore defined)

(e) where a compound of formula (VI) is formed wherein $R^1$ and $R^2$ together form a single hydroxy blocking group, treating the compound with a suitable agent to effect deblocking and selective blocking of the 5'-hydroxy group and introduction of a suitable leaving group at the 3'-position of the 5'-blocked compound.

(iii) 3'-Azidation of the 2'-deoxygenated 1-($\beta$-D-xylofuranosyl)thymine derivative (f) reacting the compound of formula (VI) with an agent serving to introduce an azido group at the 3'-position in the erythro configuration to form a compound of formula (VII)

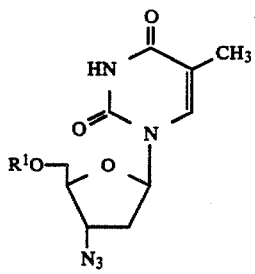

(VII)

(in which $R^1$ is as hereinbefore defined) and (g) removing the 5'-hydroxy protecting group from the compound of formula (VII) to form zidovudine.

The above procedures for the preparation of zidovudine from D-xylose are hereinafter described in more detail.

With regard to stage (a), the 1- and 2-hydroxy groups of the xylose may be blocked with an isopropylidene group, but any blocking group or groups may be used which can be selectively removed later without deblocking the 3- and 5-hydroxy groups. In the case of the isopropylidene group, blocking of the 1- and 2-hydroxy groups may be effected, for example, by the method of B. R. Baker et al. as described in J. Amer. Chem. Soc. 77, 5900 (1955). In lieu of step (a), 1,2-O-isopropylidene-$\alpha$-D-xylofuranose may be obtained commercially from the Aldrich Chemical Co. or prepared from D-glucose by the following route:

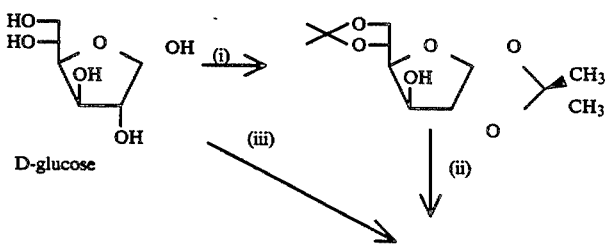

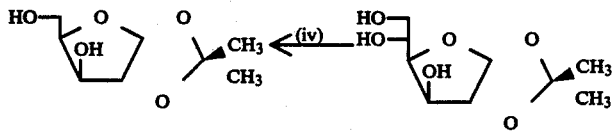

(i) Acetone/HCl (E. Fischer and C. Rund, Ber., 49, 93 (1916)) or acetone/H₃PO₄/ZnCl₂ (Methods in Carbohydrate Chemistry, R. L. Whistler and M. L. Wolfrom, Eds., II, 320 (Academic Press Inc., New York, 1963)).

(ii) Methanol/H₂SO₄ (Methods in Carbohydrate Chemistry, R. L. Whistler and M. L. Wolfrom, Eds., II, 322 (Academic Press Inc., New York, 1963)).

(iii) Acetone/H₂SO₄ (Methods in Carbohydrate Chemistry, R. L. Whistler and M. L. Wolfrom, Eds., II, 322 (Academic Press Inc., New York, 1963)).

(iv) (1) NaIO₄ (2) NaBH₄ (Synthetic Methods in Nucleic Acid Chemistry, W. W. Zorbach and R. S. Tipson, Eds., I, 195 (John Wiley & Sons, New York, 1968)).

With regard to stage (b), the 3- and 5-hydroxy groups are preferably blocked with acyl groups or a methoxycarbonate group, but any blocking groups or group may be used which are/is unaffected by the conditions employed to deblock the 1- and 2-hydroxy groups in option (i). In the case of acyl groups, blocking of the 3- and 5-hydroxy groups may be effected, for example, by reacting the compound of formula (II) with an appropriate acyl halide (e.g. chloride) or anhydride, typically in an apolar solvent such as methylene chloride in the presence of bases such as triethylamine and 4-dimethylaminopyridine or in a basic solvent such as pyridine. Suitable acyl blocking groups include acetyl, benzoyl and pivaloyl, the latter being preferred. For pivaloyl blocking groups, the preferred reagent is trimethyacetyl chloride. An alternative blocking group is benzyl, in which case the preferred reagent is a benzyl halide, e.g. benzyl chloride.

With regard to stage (b) option (i), the selective deblocking of the 1- and 2-hydroxy groups may be effected, for example, by heating the 3- and 5-protected compound in an aprotic solvent in the presence of an acid catalyst. For the case where A/B is isopropylidene and the 3- and 5-protecting groups are pivaloyl groups, selective deblocking may be effected, for example, by refluxing the compound in a mixture of dioxan and 2% aqueous sulphuric acid. Formation of the cyclic sulphite may be effected, for example, by reacting the 1-, 2-deprotected compound with thionyl chloride or thionyl bromide in an aprotic solvent such as ether in the presence of a base such as pyridine.

With regard to stage (c), the activating groups of the thymine derivative of formula (III) are preferably trimethylsilyl groups, but any suitable blocking groups may be used which can be selectively removed during the course of base/sugar linking without deblocking the 3'L - and 5'-hydroxy groups of the xylofuranosyl moiety. In the case of trimethylsilyl group, blocking of the hydroxy groups of thymine may be effected, for example, by refluxing the thymine in hexamethylenedisilazane in the presence of ammonium sulphate or by refluxing in bis(trimethylsilyl)acetamide (BSA) or by heating the thymine with trimethylsilyl chloride in an aprotic solvent such as benzene in the presence of a base such as triethylamine.

The reaction of the cyclic sulphite protected sugar moiety and the protected thymine derivative of formula (III) to form the compound of formula (IV) may be effected, for example, by heating the two compounds under nitrogen at an elevated temperature for several hours, typically at a temperature of from 80° to 150° C. for a period of from 1 to 144 hours, and treating the product, preferably in situ, with an agent which selectively deblocks the hydroxy groups of the thymine moiety without deblocking the 3'- and 5'-hydroxy groups of the xylofuranosyl moiety to give the compound of formula (IV). For the case where X and Y are trimethylsilyl groups, selective deblocking may be effected, for example, by treatment with a polar solvent such as NaHCO₃ in methanol.

Deblocking of the 3'- and 5'-hydroxy groups of the xylofuranosyl moiety may be effected, for example, by treating the compound of formula (IV) with ammoniacal alcohol, typically at a temperature of from 0° C. to room temperature, or with a Group I or II metal alkoxide, carbonate, or bicarbonate (or two or more thereof) in a polar solvent such as methanol, typically at a temperature of from 0° C. to reflux, and neutralising the product, for example, with an acidic resin.

With regard to stage (d) option (i), the 3'- and 5'-hydroxy groups are preferably blocked by a ketal group, for example, an acetonide group, or other such groups including, for example, cyclic carbonate, and silyl ether groups, e.g. tetraisopropyldisiloxan-1,3-diyl. In the case of an acetonide group, blocking may be effected, for example, by reaction with acetone, advantageously in the presence of a strong organic or inorganic acid such as hydrochloric acid and preferably in the presence of 2,2-dimethoxypropane. In the case of the tetraisopropyldisiloxan-1,3-diyl group, blocking may be effected, for example, by reaction with 1,3-dichloro-1,1,3,3-tetraisopropyldisiloxane using the method described by W. T. Markiewicz and M. Wiewiorowski in "Nucleic Acid Chemistry", Part 3, L. B. Townsend and R. S. Tipson, Eds., John Wiley and Sons, New York (1986).

(1) The leaving group is advantageously an organosulphonyloxy group, for example, an alkyl- or arylsulphonyloxy group such as methanesulphonyloxy, p-toluenesulphonyloxy, or p-trifluoromethyl sulphonyloxy, the compound being typically prepared by treatment of a precursor with an appropriate acid halide (e.g. chloride) or anhydride, advantageously at room temperature in the presence of an aprotic base such as pyridine.

(2) The cyclisation of the compound is generally effected in the presence of K₂CO₃ or a strong base such as 1,8-diazabicyclo[5,4,0]undec-7-ene (DBU) or 1,5-diazabicyclo[4.3.0]non-5-ene (DBN), conveniently in a polar aprotic solvent such as dimethylformamide or acetonitrile. The reaction may also be carried out in the presence of NaHCO₃ in a protic solvent, such as methanol or ethanol.

(2 option b) The compound is treated with an agent serving to introduce a reduceable group at the 2'-position. The group is advantageously a halo atom, particularly bromo or iodo, but may alternatively be a thio (—SH), alkylthio (—SR in which R is a $C_{1-6}$ alkyl group), or arylthio group (e.g. phenyl optionally substituted by $C_{1-6}$ alkyl or $C_{1-6}$ alkoxy). The halo group may be introduced by treatment of the compound with an inorganic halide, for example, an alkali metal bromide such as sodium or lithium bromide, or an acyl bromide, for example, acetyl or benzoyl bromide, in which latter case the 3'- and 5'-blocking groups are thereby converted to the corresponding acyl blocking groups, or by reaction with a hydrohalide salt of a tertiary amine, for example, pyridine hydrobromide. The reaction is generally effected in an appropriate organic solvent, for example, acetonitrile or dimethyl formamide, but acetic acid is the preferred solvent when using acetyl bromide.

The resulting compound is then preferably deblocked at the 3'- and 5'-positions, for example, by hydrolysis. In the case of a ketal blocking group, the hydrolysis is advantageously effected under acidic conditions, for example, in the presence of a strong acid such as hydrochloric acid. In the case of ester blocking groups such as acyl or cyclic carbonate blocking groups, the hydrolysis is advantageously effected under basic or acidic conditions, for example using hydrogen chloride in a solvent such as methanol, while in the case of silyl ether groups, such hydrolysis may be effected, for example, using tetrabutylammonium fluoride.

The reduction of the resulting compound particularly when the reduceable group is a halo atom and preferably when deblocked as described above, is conveniently effected by catalytic hydrogenation, for example in the presence of a palladium catalyst. When the reduceable group is a thio or alkylthio group, reduction is advantageously effected by hydrogenation in the presence of Raney nickel.

Alternatively, if 3'- and 5'-deblocking is not effected before the reduction step it can be carried out after reduction, for example, by appropriate hydrolysis as described above.

In a modification of the process outlined above, a compound wherein the 2'- leaving group is a group of formula —OCSOR or —OCSSR (in which R represents a $C_{1-4}$ alkyl group, e.g. methyl, or aryl group, e.g. phenyl) or —COCOOCH$_3$, may be converted directly to a 2'-deoxy compound by the Barton Reaction (D. H. R. Barton et al., J. Chem. Soc., Perkin Transactions I, 1574 (1975), for example by treatment with a trialkyl (e.g. methyl) tin hydride in the presence of an initiator such as azoisobutyronitrile (AIBN).

With regard to step (d), (i) a compound of formula (IV) may be deblocked by for example hydrolysis and treated to block the 3'- and 5'-hydroxy groups of 1-($\beta$-D-xylofuranosyl)thymine by a tetraisopropyldisiloxan-1,3-diyl group, for example, by reaction with 1,3-dichloro-1,1,3,3-tetraisopropyldisiloxane using the method of Markiewicz and Wiewiorowski referred to above. Blocking by an aliphatic ketal group (as defined) may be effected by reaction with the appropriate ketone, for example, acetone in the case of the isopropylidine group, advantageously in the presence of a strong organic or inorganic acid such as hydrochloric acid and preferably in the presence of 2,2-dimethoxypropane.

Alternatively with regard to step (d), (i), (2a) the preparation of compounds of formula (V) is effected as hereinbefore described, the opening of the anhydro ring being effected by base hydrolysis, preferably in the presence of dilute aqueous sodium hydroxide.

With regard to step (d), (i), (2b) the reduceable group is introduced to the 2'-position of a compound of formula (IV) or (V) and is advantageously a benzoate or substituted benzoate group, for example, a 4-chlorobenzoate or 3-trifluoromethylbenzoate group, the compounds being typically prepared by treatment of the corresponding precursor with an appropriate acid halide (e.g. chloride) or anhydride, advantageously at room temperature in the presence of an aprotic base such as pyridine.

With regard to step (d), (ii), the photolytic removal of the 2'-reduceable group is typically carried out by irradiating the compound with a high pressure mercury lamp having a Pyrex filter in the presence of an electron transfer agent such as N-methylcarbazole or N-ethylcarbazole in an aqueous/organic solvent system such as water/THF (1:10) or water/isopropanol (1:10) at about room temperature under an inert atmosphere such as nitrogen. A catalytic amount of magnesium perchlorate may optionally be present. (J. Saito et al; J. Amer. Chem. Soc. 108, 3115 (1986)).

The compound may then be deblocked at the 3'- and 5'-positions by, for example, hydrolysis. In the case of the tetraisopropyldisiloxan-1,3-diyl blocking group, hydrolysis may be effected using tetrabutylammonium fluoride, preferably in tetrahydrofuran. In the case of an aliphatic ketal blocking group (as defined), for example, the isopropylidene group, hydrolysis is advantageously effected under acidic conditions, for example, in the presence of a strong acid such as hydrochloric acid.

Alternatively, deblocking of the 3'- and 5'-hydroxy groups may occur before deoxygenation and the subsequent irradiation may be carried out using the methods described above.

With regard to step (e), the 5'-blocking agent may be an appropriate halide, for example, trityl chloride. The agent serving to introduce the leaving group in the compound may also be an appropriate halide, such as mesyl chloride. The second agent is preferably added to the 5'-blocked intermediate in situ. Where either agent is a halide, the addition is preferably made in the presence of a base such as pyridine. The introduction of the 3'-azido group (stage f) may be effected, for example, using an alkali metal azide, for example lithium or sodium azide. Finally, with regard to step (g), the deblocking of the 5'-hydroxy group may be effected, for example, by acid hydrolysis, e.g. in aqueous hydrochloric acid.

It should be appreciated that the invention is concerned not only with the overall synthetic route outlined above for the conversion of D-xylose into zidovudine, but also with the individual reaction stages. The overall synthetic route and also its novel individual stages, alone or in combination, each represent further features of the invention together with the novel intermediates referred to below.

(a) The novel compounds of formula (IV) wherein:
 (i) $R^1$ and $R^2$ are pivaloyl and $R^4$ is hydrogen;
 (ii) $R^1$ and $R^2$ together form a tetraisopropyldisiloxan-1,3-diyl group and $R^4$ is trifluoromethylbenzoyl.
(b) The novel compounds of stage (b) wherein:
 the 3- and 5-hydroxy blocking groups are pivaloyl and the 1- and 2-positions are protected by a cyclic sulphite group or are both hydroxy groups.
(c) The novel compounds of formula (VI) wherein:
 $R^1$ and $R^2$ together form tetraisopropyldisiloxan-1,3-diyl.
(d) The novel compounds of stage (d) wherein:

(i) the 3'- and 5'-hydroxy groups are blocked by an acetonide group and the 2'-position forms a cyclic link with the 2-position of the base;

(ii) the 3'- and 5'-hydroxy groups are blocked by acetyl groups and the 2'-reduceable group is bromo.

(e) The use of each and every compound listed in (a)–(e) above in the synthesis of zidovudine particularly from the starting material D-xylose.

(f) A compound as listed in (a)–(e) above for use in the synthesis of zidovudine particularly from the starting material D-xylose.

(g) A process for the preparation of zidovudine from a compound of formula (VII) wherein $R^1$ is methoxycarbonyl.

(h) A process for the preparation of zidovudine involving photochemical 2'-deoxygenation of a compound of formula (IV) wherein $R^4$ is a photolytic group.

(i) A process for the preparation of zidovudine from D-xylose involving stages (a)–(g) above, and each and every novel stage thereof.

The following Examples illustrate the present invention.

All glassware used in non-air reactions was dried in an oven overnight at 150° C. The glassware was removed from the oven and evacuated and purged with nitrogen three times. The system then remained under a nitrogen atmosphere for the duration of the experiment.

Solvents were purified as follows: Methylene chloride was freshly distilled from phosphorus pentoxide. Benzene was washed with sulphuric acid and distilled prior to use. Triethylamine was distilled one day in advance from potassium hydroxide and stored over potassium hydroxide pellets. Pyridine was distilled one day in advance from potassium hydroxide and stored over potassium hydroxide pellets. Thionyl chloride was freshly distilled from 10% w/w triphenyl phosphite. Trimethylsilyl chloride was freshly distilled before use.

EXAMPLE B1

1,2-O-Isopropylidene-α-D-xylofuranose

D-xylose was converted to 1,2-O-isopropylidene-α-D-xylofuranose by the method of B. R. Baker et al. as described in J. Amer. Chem. Soc. 77, 5900 (1955).

EXAMPLE B2

1,2-O-Isopropylidene-3,5-di-O-pivaloyl-α-D-xylofuranose

A dry 250 ml round-bottomed flask was equipped with an internal thermometer and magnetic stirring bar and maintained under a nitrogen atmosphere. The flask was charged with 1,2-O-isopropylidene-α-D-xylofuranose (9.5 g, 49.95 mmol) from Example B1, methylene chloride (70 mL), and triethylamine (8.7 mL, 62.4 mmol). The solution was cooled to an internal temperature of 3° C. using a brine/ice bath. Trimethylacetyl chloride (7.69 ml, 62.4 mmol) was added dropwise, via syringe, over a ten minute period. Finally, 4-dimethylaminopyridine (1.83 g, 14.99 mmol) was added and stirring continued for 75 minutes. The mixture was brought to room temperature and diluted with methylene chloride (70 mL). It was then extracted with water (40 mL) and brine (40 mL). The organic layer was dried over magnesium sulfate, filtered and concentrated in vacuo. The product was purified on a preparatory silica gel column eluted with 80:20 (v/v) hexane/ethyl acetate. The product was obtained as a clear colourless oil. Yield 29%.

TLC (silica gel): Rf 0.63 (80:20 hexane/ethyl acetate)
Calc: C 60.32, H 8.43 Found: C 60.25, H 8.45

EXAMPLE B3

3,5-Di-O-pivaloyl-α-D-xylofuranose

A 250 mL round-bottomed flask was charged with 1,2-O-isopropylidene-3,5-di-O-pivaloyl-α-D-xylofuranose from Example B2, dioxane (75 mL), and 2% aqueous sulfuric acid (45 mL). The turbid solution was heated at reflux for four hours. The solution was then cooled to room temperature and neutralized using solid sodium bicarbonate. The mixture was concentrated and dried in vacuo. The product was purified using a silica gel flash chromatography column. The product was obtained as a clear yellow tinted oil.

TLC (silica gel): Rf 0.17 (70:30 hexane/ethyl acetate)
Calc: C 56.59, H 8.23. Found: C 56.45, H 8.25.

EXAMPLE B4

Cyclic sulphite of 3,5-di-O-pivaloyl-α-D-xylofuranose

The cyclic sulphite was prepared by the method of C. H. Gagnieu et al as described in J. Carb. Chem. 5, 153 (1986). A dry 250 mL round-bottomed flask was equipped with an internal thermometer and maintained under a nitrogen atmosphere. The flask was charged with 3,5-di-O-pivaloyl-α-D-xylofuranose (5.3 g, 16.6 mmol) from Example B3 and dry diethyl ether (30 ml). Thionyl chloride (1.21 ml, 16.6 mmol) was added and the solution cooled to 0° C. in a brine/ice bath. Pyridine (2.75 g, 34.8 mmol) in dry diethyl ether (30 mL) was added dropwise over a 10 minute period. Stirring was continued for an additional 35 minutes. The reaction mixture was filtered and the filtrate loaded on to a short silica gel flash chromatography column which was then eluted with 50:50 (v/v) hexane/ethyl acetate.

EXAMPLE B5

Nucleoside formation 2,4-Bis-O-trimethylsilylthymine was prepared by the method of T. J. Bardos et al. as described in J. Org. Chem. 34, 3806 (1969). To a dry one liter round-bottomed flask were added thymine (3.78 mg, 30 mmol, dried overnight in a vacuum oven at 60° C.), benzene (250 mL), trimethylsilyl chloride (8.5 ml, 60 mmol), and triethylamine (8.35 mL). The reaction was heated at reflux, under nitrogen, for three hours. The mixture was cooled to room temperature and filtered through a Schlenk tube. The filtrate was divided into two portions.

One portion of the 2,4-bis-O-trimethylsilylthymine and one portion of the cyclic sulphite from Example B4 were combined and the benzene distilled off under nitrogen. The two components were fused at 150° C. for seven hours under nitrogen. The reaction was cooled to room temperature and diluted with methylene chloride (25 mL) and methanol (10 mL). The solution was stirred at room temperature for 30 minutes. The reaction mixture was then concentrated in vacuo and purified on a silica gel flash chromatography column eluted with 98:2 (v/v) chloroform/methanol.

Yield: 38% from 3,5-di-O-pivolyl-α-D-xylofuranose
TLC (silica gel): Rf 0.3 (95:5 v/v chloroform/methanol)

The product was a off-white glassy solid which upon heating turned to a clear solid by 72° C. and melted at from 80° to 84° C.

EXAMPLE B6

1-(β-D-Xylofuranosyl)thymine

Fox J. J., Yung N., Davoroll J. and Brown G. B., J. Amer. Chem. Soc., 1956 78 21117. The nucleoside from Example B5 (157.6 mg, 0.37 mmol) was dissolved in methanol (3 mL) and sodium bicarbonate (21 mg, 0.25 mmol) added. The solution was heated at reflux for 70 minutes. At this point, sodium methoxide (85 mg, 1.48 mmol) was added and the solution was heated at reflux for an additional 20 minutes. The solution was then cooled to room temperature and neutralized with Dowex 50W-X8 (acid form). The resin was removed by filtration and washed with methanol. The filtrate was concentrated in vacuo to an orange-tinted foam which crystallised on purification.

Chemical Method

EXAMPLE B7

1-(3',5'-O-Isopropylidene-β-D-xylofuranosyl)thymine

Crystalline 1-(β-D-xylofuranosyl)thymine (5.2 g, 0.020 mole) from Example B6 was stirred vigorously at 20° C. in a solution of acetone (20 mL) and 2,2-dimethoxypropane (20 mL) containing concentrated hydrochloric acid (0.1 mL). After two hours, the clear solution was evaporated to afford an off-white foam (6.8 g) which crystallised from ethyl acetate (15 mL) as white crystals.

Yield: 3.4 g (57%), m.p. 179°-182° C.

The NMR spectrum was in good agreement with the proposed structure.

A considerable quantitiy of isopropylidene derivative remained in the mother liquors.

In a separate experiment, 1-(β-D-xylofuranosyl)thymine (4.4 g, 0.017 mole) from Example B6 was converted to crude isopropylidene derivative as an off-white foam (5.0 g, 98%) suitable for use in the next step.

EXAMPLE B8

1-(3',5'-O-isopropylidene-2'-O-mesyl-β-D-xylofuranosyl)thymine

The crude 3',5'-O-isopropylidene derivative (5.0 g, 0.17 mole) from Example B7 in pyridine (33 mL) was allowed to react with methanesulphonyl chloride (3 mL, 0.037 mole) at 20° C. for 1.5 hours and then at 40° C. for 1 hour. Chromatography revealed one major new product.

Evaporation of the solvent gave a yellow residue which was dissolved in chloroform (60 mL) and washed with ice cold saturated aqueous sodium hydrogen carbonate (3×20 mL) and water (1×40 mL). The chloroform solution was then dried over anhydrous magnesium sulphate. Evaporation of the solvent provided a yellow gum.

Crude yield: 7.8 g (123%)

EXAMPLE B9

1-(2,2'-Anhydro-3'5'-O-isopropylidene-β-D-xylofuranosyl)thymine

The impure 2'-O-mesylate (7.8 g, equivalent to 0.017 mole) from Example B8 was heated to 100°-110° C. in a solution of dimethylformamide and 1,8-diazabicyclo[5,4,0]undec-7-ene (4.0 mL, 0.026 mole) for 8 hours. At this time, chromatography revealed a single major new component and no starting material.

High vacuum evaporation afforded a yellow syrup which crystallized from ethyl acetate (30 mL) as fine needle crystals. After standing at 4° C. for two hours, white crystals were collected.

Yield: 3.9 g (82%)

The NMR spectrum of the compound was in good agreement with the proposed structure.

For analytical purposes, the 3.9 g of material was further purified by slurrying in hot methanol (15 mL) and cooling to 0° C.

After this procedure the weight of fine white needles of the title compound was 2.9 g, m.p. 273°-274° C.

EXAMPLE B10

1-(3',5'-Di-O-acetyl-2'-bromo-2'-deoxy-β-D-xylofuranosyl)thymine

Purified 1-(2,2'-anhydro-3',5'-O-isopropylidene-β-D-xylofuranosyl)thymine (2.6 g, 9.3 mmol) from Example B9 was heated and stirred at 100° C. in a solution of acetic acid (25 mL) and acetyl bromide (2.5 mL, 33.8 mmol). After 45 minutes, the red solution was evaporated to a red glass (4.3 g). Silica gel chromatography (70–230 mesh, 100 g) of the product using ethyl acetate:-chloroform as eluent (1:1 v/v) afforded a white foam.

Yield: 3.4 g (90%)

The compound gave a sharp, well resolved NMR spectrum in agreement with the proposed structure.

EXAMPLE B11

1-(3'5'-Di-O-acetyl-2'-deoxy-β-D-threo-pentofuranosyl)thymine

Chromatographically purified 1-(3'5'-di-O-acetyl-2'-bromo-2'-deoxy-β-D-xylofuranosyl)thymine (0.5 g, 1.23 mmol) from Example B10 in 50% aqueous methanol (8 mL) containing sodium acetate trihydrate (0.3 g) was hydrogenated over 5% palladium on barium sulphate (0.2 g) at NTP.

Over a period of 30 minutes, the vigorously stirred solution absorbed about 50 ml of hydrogen. Chromatographic examination of the reaction mixture revealed two major new products and no starting material.

After filtering and evaporation, the residue was dissolved in water (7 mL) and extracted with ethyl acetate (3×7 mL). The combined extracts were dried over anhydrous sodium sulphate and evaporated to a colourless syrup.

Crude yield: 0.32 g (79%)

The NMR spectrum of the crude syrup revealed that it consisted of approximately 70% of the required compound (by comparison with the spectrum of an authentic sample) together with an unknown compound(s).

In another experiment, the 2'-bromonucleoside (4.6 g, 11.3 mmol) from above was hydrogenated in the usual manner. Part of this material was chromatographed on silica gel (110 g) using ethyl acetate/isopropanol (10:1 v/v) as eluent.

The resulting chromatographically homogeneous sample from the column afforded an NMR spectrum in full agreement with the proposed structure.

EXAMPLE B12

1-(2'-Deoxy-β-D-threo-pentofuranosyl)thymine

Chromatographically purified 1-(3',5'-di-O-acetyl-2'-deoxy-β-D-threo-pentofuranosyl)thymine (0.3 g, 0.92 mmol) from Example B12 was warmed to 40° C. in methanolic ammonia (4 ml, 10% v/v) for three hours.

Evaporation of the solvent afforded a white foam smelling faintly of acetamide and possessing the same chromatographic Rf as an authentic sample of the desired product.

Crude yield: 0.25 g (104%)

Photochemical Method

EXAMPLE B13

1-(3′,5′-O-Isopropylidene-β-D-xylofuranosyl)thymine

A 250 mL round-bottomed flask was charged with 1-(β-D-xylofuranosyl)thymine (5.2 g, 20 mmol), acetone (20 mL) from Example B6, and 2,2-dimethoxypropane (20 ml). To this solution was added conc. HCl (0.1 mL). After stirring for two hours at room temperature, the solution was neutralized with potassium carbonate. The brown solution was then filtered and concentrated in vacuo to give a white solid (6.9 g). The crude product was absorbed onto 20 g of silica gel and loaded onto a 140 g silica gel flash column. The column was initially eluted with ethyl acetate/hexanes (4:1 v/v) to remove a minor impurity, followed by ethyl acetate. Fractions containing the product were concentrated in vacuo to give a white solid.

Yield: 5.9 g (99%), m.p. 179°–181° C.

TLC (silica gel): Rf 0.19 (4:1 v/v ethyl acetate/hexanes)

EXAMPLE B14

1-(3′,5′-O-Isopropyldene-2′-O-p-trifluoromethylbenzoyl-β-D-xylofuranosyl)thymine A dry 250 mL 3-necked round-bottomed flask was charged with the nucleoside from Example B13 4.77 g, 16 mmol), dry methylene chloride (70 mL), and dry triethylamine (3.6 mL, 24 mmol) under nitrogen. The solution was cooled in an ice bath and 3-(trifluoromethyl)benzoyl chloride (5 g, 24 mmol) was added dropwise over a 10 minute period. DMAP (880 mg, 7.2 mmol) was then added, whereupon a white precipitate was obtained. After stirring for 35 minutes, methylene chloride (160 mL) was added and the resulting solution washed with satd. aqu. sodium bicarbonate (1×50 mL) and brine (1×50 mL), then dried over anhy magnesium sulphate, filtered and concentrated in vacuo. The crude product was absorbed onto 20 g of silica gel and loaded onto a 250 g silica gel flash column. The column was eluted with chloroform, followed by chloroform/methanol (90:10 v/v). Fractions containing the product were concentrated in vacuo to give a white solid.

Yield: 79% m.p. 205°–207° C.

TLC (silica gel): Rf 0.54 (95:5 v/v chloroform/methanol)

EXAMPLE B15

1-(3′,5′-O-Isopropylidene-2′-deoxy-β-D-threo-pentofuranosyl)thymine

A solution of the nucleoside from Example B14 (806 mg, 1.71 mmol) and N-methylcarbazole (336 mg, 1.82 mmol) in isopropanol/water (10:1 v/v, 286 mL) was irradiated with an Hanovia 450W high pressure mercury lamp through a Pyrex filter under nitrogen at room temperature for 4 hours. The solution was then concentrated in vacuo and the residue dissolved in methylene chloride. The resulting solution was washed with satd. aqu. sodium bicarbonate (2×100 mL), dried over anhy. magnesium sulphate, filtered and concentrated in vacuo to give a yellow-brown oil. The crude product was absorbed onto 6 g of silica gel and loaded onto a 44 g flash column. The column was eluted with chloroform/methanol (98:2 v/v). Fractions containing the product were concentrated in vacuo to give a white solid.

Yield: 83.5%

TLC (silica gel): Rf 0.42 (95:5 v/v chloroform/methanol)

EXAMPLE B16

1-(2′-Deoxy-β-D-threo-pentofuranosyl)thymine

The nucleoside from Example B15 (403.3 mg, 1.43 mmol), Dowex 50W-X8 (H+ form, 2.5 g), and water (20 mL) were heated at 70° C. for 1 hour. The mixture was then cooled in an ice bath and the resulting resin filtered off. The filtrate was concentrated in vacuo to give a brown solid (99% yield). This material was absorbed onto 1 g of silica gel and loaded onto a 7 g flash column. The column was eluted with chloroform/methanol (95:5 v/v) and the eluate concentrated in vacuo. Impure fractions were re-chromatographed. The product was obtained as a white crystalline solid.

Yield: 70%, m.p. 166°–167° C. (lit. m.p. 168°–169° C.)

TLC (silica gel): Rf 0.27 (90:10 v/v chloroform/methanol)

EXAMPLE B17

1-(2′-Deoxy-3′-O-mesyl-5′-O-trityl-β-D-threo-pentofuranosyl)thymine

Impure 1-(2′-deoxy-β-D-threo-pentofuranosyl)thymine (0.49 g, 2.0 mmol) from Example B16 in pyridine (8 ml) was treated with trityl chloride (0.75 g, 2.7 mmol) at 40° C. for five hours. The solution was cooled to 10°–15° C., mesyl chloride (0.23 mL, 3.0 mmol) was introduced, and the temperature maintained at 10°–15° C. for 16 hours. Standard isolation procedures afforded a pale yellow solid which crystallized from ethyl acetate as off-white crystals.

Yield: 0.87 g (75%)

Chromatographic and NMR data for the compound were in full agreement with an authentic sample of the title compound.

EXAMPLE B18

1-(3′-Azido-2′,3′-dideoxy-5′-O-trityl-β-D-erythro-pentofuranosyl)thymine

Crystalline 1-(2′-deoxy-3′-O-mesyl-5′-O-trityl-β-D-threo-pentofuranosyl)thymine (0.80 g, 1.4 mmol) from Example B17 was stirred in a solution of DMF (6 mL) in the presence of sodium azide (0.10 g, 1.54 mmol) at 95° C. for 4.5 hours.

The product was isolated by firstly destroying excess azide ions with sodium nitrite (0.10 g, 1.5 mmol) dissolved in a solution of 20% aqueous acetic acid (2 mL) by stirring for one hour at 20° C. Additional aqueous acetic acid (12 mL) was then added to precipitate the product which was isolated by filtration and drying.

Crude yield: 0.60 g (84%)

The 3′-azido derivative was characterised by the usual analytical techniques.

EXAMPLE B19

1-(3'-Azido-2',3'-dideoxy-β-D-erythro-pentofuranosyl)thymine (zidovudine)

Crude 1-(3'-azido-2',3'-dideoxy-5'-O-trityl-β-D-erythro-pentofuranosyl)thymine (0.60 g, 1.2 mmol) from Example B18 was suspended in a solution of 50% aqueous methanol (5 mL) adjusted to pH 2.0 with hydrochloric acid, and refluxed for 4 hours. On cooling to 20° C., triphenylmethanol crystallised out and was removed by filtration. The mother liquors were evaporated to remove most of the alcohol. On cooling to 10° C., zidovudine crystallized from solution as a white solid.

Yield: 0.25 g (76%)

The product was shown to be identical in every respect with an authentic sample of zidovudine.

We claim:

1. A compound of formula

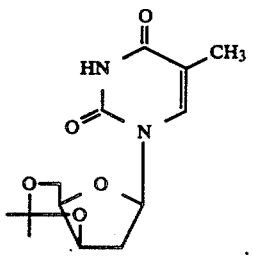

2. A compound of formula

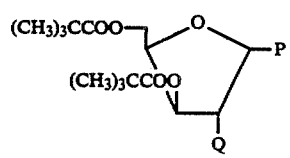

wherein P and Q are both hydroxy groups or together form a cyclic sulphite group.

* * * * *